(12) United States Patent
Severinkangas et al.

(10) Patent No.: US 10,234,340 B2
(45) Date of Patent: Mar. 19, 2019

(54) MULTILAYER STRUCTURE FOR CAPACITIVE PRESSURE SENSING

(71) Applicant: TactoTek Oy, Oulunsalo (FI)

(72) Inventors: Kari Severinkangas, Oulu (FI); Mikko Heikkinen, Oulu (FI); Jarmo Saaski, Kempele (FI)

(73) Assignee: TACTOTEK OY, Oulunsalo (FI)

(*) Notice: Subject to any disclaimer, the term of this patent is extended or adjusted under 35 U.S.C. 154(b) by 122 days.

(21) Appl. No.: 14/677,075

(22) Filed: Apr. 2, 2015

(65) Prior Publication Data

US 2016/0290878 A1    Oct. 6, 2016

(51) Int. Cl.
*G01D 7/08* (2006.01)
*G01L 3/00* (2006.01)
(Continued)

(52) U.S. Cl.
CPC .......... *G01L 1/146* (2013.01); *A61B 5/1038* (2013.01); *A61B 5/112* (2013.01); *A61B 5/6807* (2013.01);
(Continued)

(58) Field of Classification Search
CPC .......... G01L 1/146; H05K 2203/1305
(Continued)

(56) References Cited

U.S. PATENT DOCUMENTS

| | | | |
|---|---|---|---|
| 7,735,383 B2 * | 6/2010 | Dattalo et al. | G01D 5/2405 73/780 |
| 2007/0128920 A1 * | 6/2007 | Brown et al. | H01R 43/0263 439/440 |

(Continued)

FOREIGN PATENT DOCUMENTS

| | | |
|---|---|---|
| DE | 102011012458 | 8/2012 |
| EP | 2053907 A2 | 4/2009 |

OTHER PUBLICATIONS

Authors: Bo Zhang, Zemin Xiang, Siwei Zhu, Qiyi Hu, Yuanzhi Cao, Junwen Zhong, Qize Zhong, Bo Wang Yunsheng Fang, Bin Hu, Jun Zhou, and Zhonglin Wang, Title: Dual functional transparent film for proximity and pressure sensing, Publication: Nano Research, 7(10), Date: 2014, : pp. 1488-1496.*

(Continued)

*Primary Examiner* — Lisa M Caputo
*Assistant Examiner* — Roger G Hernandez-Prewitt
(74) *Attorney, Agent, or Firm* — Robert P. Michal, Esq.; Carter, DeLuca, Farrell & Schmidt, LLP

(57) ABSTRACT

A multilayer structure for a garment, optionally footwear, includes a flexible substrate film for accommodating electronics, a number of flexible sensor pads provided on the film utilizing printed electronics technology, optionally screen printing or ink jetting, at least one electronic circuit, preferably integrated circuit, further provided on the film for controlling capacitive measurements via the number of sensor pads for obtaining an indication of pressure subjected to the multilayer structure, a number of conductor traces further printed on the film for electrically connecting the at least one electronic circuit and the number of capacitive sensor pads, a power supply element for powering electricity-driven components including the at least one electronic circuit, and at least one plastic layer molded upon the film substantially embedding the number of sensor pads, conductor traces and the at least one electronic circuit therewithin. A related method of manufacture is presented.

16 Claims, 4 Drawing Sheets

(51) Int. Cl.
*G01L 1/14* (2006.01)
*H05K 3/10* (2006.01)
*A61B 5/103* (2006.01)
*A61B 5/11* (2006.01)
*A61B 5/00* (2006.01)
*H05K 1/18* (2006.01)
*H05K 3/28* (2006.01)

(52) U.S. Cl.
CPC ............... *H05K 1/189* (2013.01); *H05K 3/10* (2013.01); *H05K 3/284* (2013.01); *H05K 2201/10037* (2013.01); *H05K 2201/10098* (2013.01); *H05K 2201/10151* (2013.01); *H05K 2203/1305* (2013.01)

(58) Field of Classification Search
USPC ............................................. 73/780, 862.046
See application file for complete search history.

(56) References Cited

U.S. PATENT DOCUMENTS

| | | | |
|---|---|---|---|
| 2008/0202251 A1* | 8/2008 | Serban et al. .......... | G01L 1/142 73/780 |
| 2009/0073130 A1* | 3/2009 | Weber et al. ....... | G06F 3/03547 345/173 |
| 2010/0274447 A1* | 10/2010 | Stumpf .................... | G01D 1/00 701/36 |
| 2011/0199340 A1* | 8/2011 | Aikio et al. ......... | G02B 6/0021 345/175 |
| 2012/0069536 A1* | 3/2012 | Sporon-Fiedler et al. ................. | H05K 1/111 361/760 |
| 2013/0176746 A1* | 7/2013 | Nishimura et al. .... | H05K 1/189 362/382 |
| 2014/0135954 A1* | 5/2014 | Vranish ................... | A43D 1/02 700/91 |
| 2014/0174205 A1 | 6/2014 | Clarke et al. | |
| 2015/0018721 A1 | 1/2015 | Wang et al. | |

OTHER PUBLICATIONS

Author: Bryce Osoinach, Title: Proximity Capacitive Sensor Technology for Touch Sensing Applications, Date: 2008, Publisher: Freescale Semiconductor, pp. total: 12.*
Author: Jonathan William Huber, Title: Dynamic Mutual Capacitive Sensor for Human Interactions., Date: 2013, Publisher: University of Tennessee, Graduate School at Trace: Tennessee Research and Creative Exchange, Total pp. 77.*
Author: unknown, Title: SMD-Surface Mount Device, Date: 2018, Publication: EUROCIRCUITS TV, pp. 1.*
International Search Report, dated Sep. 2, 2016, from corresponding PCT application No. PCT/FI2016/050204, Finnish Patent and Registration Office, pp. total: 5.
Sergio, M et al. "A Textile Based Capacitive Pressure Sensor", IEEE Conference Publications, Sensors, 2002. Proceedings of IEEE vol. 2, Year 2002, pp. 1625-1630.
Dinh, T.H.N. et al. "Polymer-based flexible capacitive pressure sensor for non-invasive medical monitoring applications", IEEE Conference Publications, Medical Measurements and Applications (MeMeA), Year 2014, pp. 1-5.
Narakathu, B.B. et al. "A Novel Fully Printed and Flexible Capacitive Pressure Sensor", IEEE Conference Publications, Sensors, 2012 IEEE, Year 2012, pp. 1-4.
Li, Y et al. "An all-inkjet printed flexible capacitor on a textile using a new poly(4-vinylphenol) dielectric ink for wearable applications", IEEE Conference Publications, Sensors, 2012 IEEE, Year 2012, pp. 1-4.
Extended European Search Report issued by the European Patent Office in relation to European Application No. 16771459.1 dated Dec. 4, 2018 (9 pages).

* cited by examiner

MULTILAYER STRUCTURE FOR CAPACITIVE PRESSURE SENSING

FIELD OF THE INVENTION

Generally the present invention relates to electronics, electronic devices, associated structures and methods of manufacture. In particular, however not exclusively, the present invention concerns wearable technology incorporating sensing electronics.

BACKGROUND

Wearable technology such as smart clothing fuses textiles and electronics to make a wearer's life easier by implementing different aspects of ubiquitous computing for both private and business purposes. Recent advancements in material technology and miniaturization have brought forward solutions that the users have only dreamed about a decade or two ago. Hard shell wearable technology such as various smart watches or generally wristop devices has been limitedly available for some time now starting from the 80's wristop calculator watches evolving into sports/fitness computers, activity monitors and most recently, various communications-enabled apparatuses approaching e.g. cell phones and tablets in terms of embedded features. Yet, few wearable smartglasses and e.g. personal security—related products have since hit the markets.

E-textiles or 'smart textiles' refer to fabrics that provided for integration with electronics such as sensory integration. The e-textiles may incorporate both electrically conductive materials, such as conductive yarn, and insulating materials for providing the desired electrical properties to the components embedded therewithin.

Also footwear such as shoes, boots, socks, insoles, etc. may benefit from the advent of wearable electronics and smart clothing. As with other garments, the footwear may be provided with integrated electrical components such as processor, memory, communication interface, and a sensor.

FIG. 1 illustrates one example of a possible multilayer structure 100 for constructing smart insoles or soles for shoes provided with a sensing functionality. The various layers of the structure have been depicted as physically separate from each other for clarity purposes only.

The structure 100 may incorporate a base part or base substrate 102 that may be provided with electronics. For instance, the base 102 may be provided with recesses for accommodating electronic components. Further layers are provided onto the base. Such layers include insulation layers 104, 108 and sensing layers 106, 110 that together form a pressure sensor. Protective layers 112 may be provided on top to protect the underlying features from potentially detrimental effects of the environment such as external impacts, moisture, dirt, etc. The established sensor detects capacitance change due to a pressure imposed on the multilayer structure by the foot of the wearing person, hereinafter user, causing compression of e.g. the insulating layer 108 between the sensing layers 106, 110. The distance between the layers 106, 110 acting as capacitor plates is thus responsive to the pressure and affects the sensed capacitance between the plates. Perhaps even in a greater majority of similar products, separate force-sensitive resistive sensors have been deployed for sensing the pressure caused by the user's movements.

Notwithstanding the various functional benefits the above-described sole structure may admittedly offer over a variety of more traditional passive insoles having regard to e.g. monitoring capability of mechanical pressure induced thereto, there still seems to remain some room for improvement.

The obtained structure may easily turn out somewhat stiff and thick, which is understandable when a considerable number of material layers having electronic components, conductors, etc. embedded therewith are joined together with necessary electrical, insulation, accommodation and protective capabilities, but still undesirable in terms of a limited space available in the target footwear and user discomfort arising from the material selections and related parameters such as stiffness/rigidity and even weight.

SUMMARY

The objective of the present invention is to at least alleviate one or more of the above defects associated with existing solutions in the context of wearable technology incorporating sensing electronics for monitoring a number of predefined parameters associated with the user's motion.

The objective is achieved with embodiments of a multilayer structure and related method of manufacture in accordance with the present invention.

According to one aspect of the present invention, a multilayer structure for a garment, optionally footwear, comprises a flexible substrate film for accommodating electronics, a number of flexible sensor pads provided on the film utilizing printed electronics technology, optionally screen printing or ink jetting, at least one electronic circuit, preferably integrated circuit, further provided on the film for controlling capacitive measurements via the number of sensor pads for obtaining an indication of pressure subjected to the multilayer structure, a number of conductor traces further printed on the film for electrically connecting the at least one electronic circuit and the number of capacitive sensor pads, a power supply element for powering electricity-driven components including the at least one electronic circuit, and at least one plastic layer molded upon the film substantially embedding the number of sensor pads, conductor traces and the at least one electronic circuit therewithin.

In one embodiment, the at least one electronic circuit, such as a microcontroller, microprocessor, or a signal processor, has been configured to sense the capacitance between the pads and external elements, typically the sole of the user, placed on the structure. While the foot and specifically sole of the user depresses the top surface of the structure downwards and causes deformation of the underlying material, the sole and one or more of the pads also establish a capacitor the capacitance of which may be sensed by the electronics. Capacitance is dependent on the distance between the sole and the pad(s), being thus indicative of e.g. the amount of pressure subjected to the structure.

Optionally, a plurality of pads may be formed on the surface of the substrate e.g. adjacent to each other or in some other preferred configuration so that capacitance/pressure data may be collected with spatial resolution, i.e. at multiple locations corresponding to the locations of the pads. Accordingly, e.g. capacitance or pressure distribution may be spatially determined in terms of different locations on the substrate film.

In one other, either supplementary or alternative, embodiment, the at least one electronic circuit has been encapsulated by at least two overlapping plastic layers provided sequentially thereon. The latter layer may cover more elements and/or more of the surface (area) of the film than the first layer. The first layer may in some embodiments may be first established to cover and protect the at least one electronic circuit, whereupon the second layer is formed to cover the film more including e.g. the sensor pads and conductors as well.

In a further, either supplementary or alternative, embodiment the structure comprises a sub-assembly or sub-unit including the at least one electronic circuit initially provided on a secondary substrate, optionally FPC (Flexible Printed Circuit). The sub-assembly has been thus pre-manufactured at least partially separately from the remaining multilayer structure and ultimately mounted onto the flexible substrate film with necessary mechanical and electrical connections to other elements such as sensor pads thereon, which may have necessitated the use of adhesive and/or soldering. Optionally the aforesaid first molded layer may have been provided upon the at least one electronic circuit and optionally the secondary substrate prior to displacement on the flexible substrate film.

Still in a further, either supplementary or alternative, embodiment the at least one electronic circuit further comprises a number of passive and/or active components. For example, a resistor, capacitor, inductor/coil, diode, LED (light-emitting diode), and/or a transistor may be provided.

Yet in a further embodiment, the structure further comprises an accelerometer.

In a further embodiment, the structure further comprises protective element or protective layer disposed upon the traces. For example, adhesive tape may be utilized for the purpose.

In a further embodiment, the at least one electronic circuit is at least partially established utilizing printed electronics technology. Alternatively or additionally, e.g. surface mount components (SMT, surface-mount technology) may be used.

In a further embodiment, the structure further comprises a user interface. The user interface may include at least one element selected from the group consisting of: touch interface, touch-sensitive area, capacitive touch-sensitive area, button, switch, display, indicator light, and indicator LED.

In a further embodiment the structure further comprises a data interface for communicating with at least one external element, optionally selected from the group consisting of: a tablet, phablet, cell phone, wristop device, smartwatch, smartgoggles, computer, desktop computer, network infrastructure, network element, and a laptop computer. The data interface may be wireless or wired.

In a further embodiment, the at least one electronic circuit includes a memory for storing instructions and/or data. The data may include sensor data or data based on sensor data, e.g. capacitance data, pressure data and/or acceleration data.

In a further embodiment, the power supply element may include a battery, optionally a rechargeable battery, or at least a connector therefor. In addition or alternatively, the power supply element may include a wiring and/or connector for coupling with external power supply. The external power supply may include an external battery, which may be of rechargeable or disposable type.

An insole or sole for footwear comprising an embodiment of the multilayer structure may be provided.

Headwear such as a helmet comprising an embodiment of the multilayer structure may be provided.

A compression or stretch garment comprising an embodiment of the multilayer structure may be provided.

According to one other aspect, a method for manufacturing a multilayer structure for a garment, optionally footwear, comprises obtaining a flexible substrate film for accommodating electronics, printing a number of flexible sensor pads on the film utilizing printed electronics technology, optionally screen printing or ink jetting, printing a number of conductor traces on the film for electrically connecting at least said sensor pads with an electronic circuit, providing the electronic circuit, preferably integrated circuit, on the film for controlling capacitive measurements via the number of sensor pads for obtaining an indication of pressure subjected to the multilayer structure, providing a power supply element for supplying electricity-driven components including the electronic circuit with electricity, and molding at least one plastic layer upon the film substantially embedding the number of sensor pads, conductor traces and the at least one electronic circuit therewithin.

Depending on the embodiment of the method, also the power supply element may be connected to the electronic circuit via the printed conductor traces. Alternatively, other conductors (e.g. wires) may be utilized for the purpose.

The method may further comprise at least one item selected from the group consisting of: provision of an secondary, optionally flexible, substrate and securing at least the electronic circuit first thereon for subsequent placement as a sub-assembly on the flexible substrate film, initial over-molding of the electronic circuit prior to over-molding it and the sensor pads on the flexible substrate film, provision of an accelerometer on the flexible substrate film, covering one or more of the sensor pads and/or traces with protective element or layer prior to molding, and provision of one or more additional layers upon the overmolded flexible substrate structure.

The utilized molding method may include injection molding, for instance.

The previously presented considerations concerning the various embodiments of the structure may be flexibly applied to the embodiments of the method mutatis mutandis, and vice versa, as being appreciated by a skilled person.

The utility of the present invention arises from a plurality of issues depending on each particular embodiment thereof. The obtained multilayer structure may be integrated with other elements or a host device to implement the desired construction. The structure may generally remain flexible, thin, light and affordable, which are all factors positively extending the usability of the solution in various contexts such as in connection with footwear, headwear or other garments. The other garments may include e.g. shirts (e.g. compression shirts), jackets, trousers, etc. In compression garments, for example, that are usually designed for medical or sports use, or occasionally both, the structure may offer additional wearing convenience (affected by snug fit or direct skin contact of the garment with the body of the user, whereupon the thinness, lightness, and flexibility of the structure is beneficial) and even functional reliability (in terms of sensing body capacitance, for example) over more traditional and e.g. more loose solutions.

The use of several overlapping, stacked sensing layers having insulating materials in between may be omitted as the external element such as body (sole skin) of the user facing the structure may be utilized as one capacitor plate in addition to at least one embedded printed conductive pad area on the flexible substrate. The structure may be provided with a number of additional layers, each with desired properties having regard to e.g. insulation, flexibility/rigidity, cushioning, etc. The structure may be shaped and/or cut to fit the target environment (use location, e.g. shoe of certain inner dimensions) with the necessary accuracy. Application of printed electronics technology provides for flexible and relatively simple positioning of e.g. sensor pads and conductor traces on the substrate. Even more complex, potentially active, components may be similarly provided. The embedded electronics remains protected from external events such as impacts, moisture, heat/cold or generally extreme temperatures or temperature changes, dirt, etc.

In addition to capacitive sensing that may be harnessed for measuring pressure, for instance, other measurements and/or calculations may be conveniently executed. The obtained sensor data may be utilized to determine various characteristics of the wearing person's movement such as gait, stance, step length, step count, etc.

The expression "a number of" may herein refer to any positive integer starting from one (1).

The expression "a plurality of" may refer to any positive integer starting from two (2), respectively.

Different embodiments of the present invention are disclosed in the attached dependent claims.

BRIEF DESCRIPTION OF THE DRAWINGS

Next the present invention will be described in greater detail with reference to the accompanying drawings, in which.

DETAILED DESCRIPTION

Figure 1:
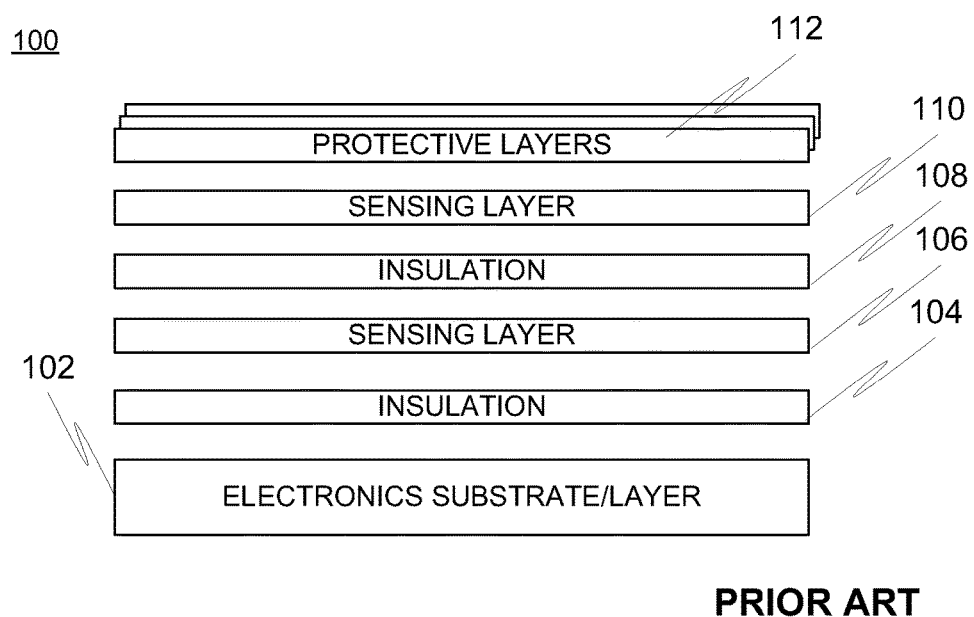
FIG. 1 illustrates one example of a multilayer structure.

FIG. 1 was already contemplated hereinbefore.

Figure 2:
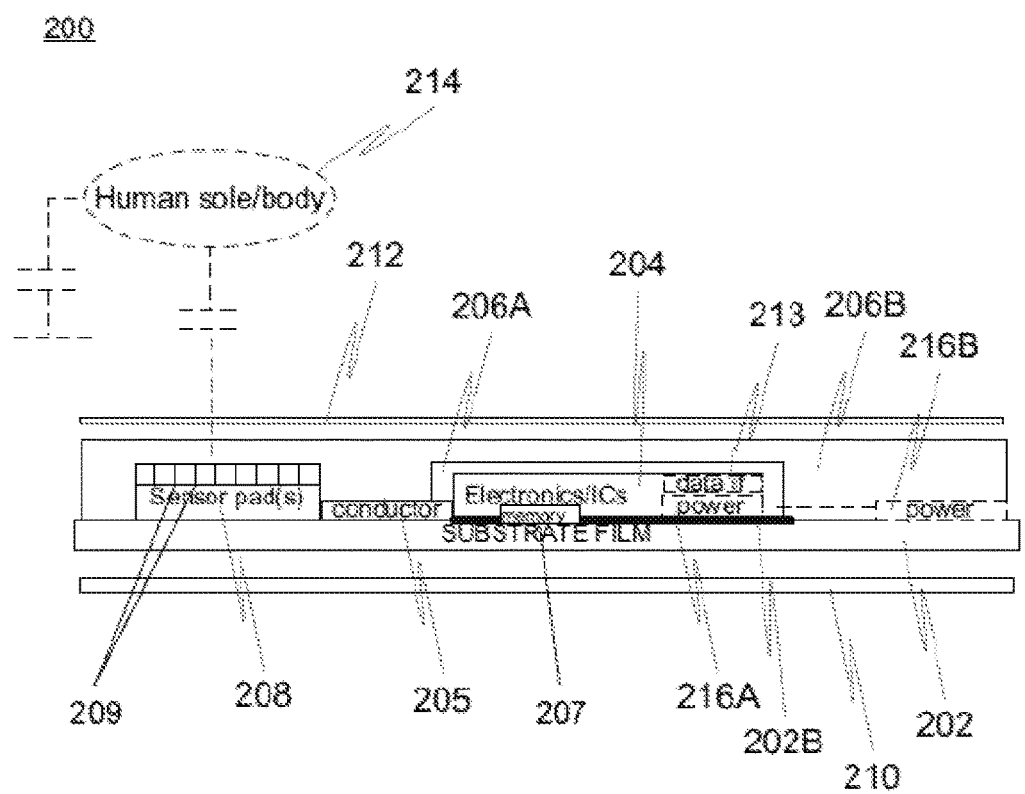
FIG. 2 is a cross-sectional side view of an embodiment of a multilayer structure in accordance with the present invention.

FIG. 2 depicts, at 200, a cross-sectional side view of an embodiment of a multilayer structure in accordance with the present invention.

The construction comprises a flexible substrate film, or 'foil', 202 typically but not necessarily of plastics. For example, the film 202 may substantially consist of or at least comprise one material selected from the group consisting of: polymer, thermoplastic material, PMMA (Polymethyl methacrylate), Poly Carbonate (PC), polyimide, a copolymer of Methyl Methacrylate and Styrene (MS resin), glass and Polyethylene Terephthalate (PET).

The used materials and their proportion naturally affect e.g. the flexibility of the film 202, which should be taken into account when selecting the materials in addition to other potentially relevant factors. For example, in some embodiments optical transmittance of the material may be relevant if e.g. light-emitting device such as LED or OLED (organic LED) is provided thereon for indication or illumination purposes and the emitted light should penetrate the film. Alternatively or additionally, a light-sensitive element such as a detector could be provided. These aspects may have to be considered on case-by-case basis. So the film may be optically substantially transparent, translucent or opaque depending on the embodiment having regard to predefined wavelengths.

The dimensions and thickness of the film 202 may vary from an embodiment to another. For example, if embedded in a shoe sole or insole, or other garment, the width and length of the substantially planar film may be in the order of magnitude of few tens or hundreds of millimeters. The shape of the film 202 may be generally configured to follow or conform to the ones of the target location, e.g. shoe internals and/or foot sole forms. The thickness may vary as well, even within the same embodiment. It may only be one or few tens of a millimeter, about one millimeter or even several millimeters, for instance.

The substrate 202 may be shaped according to the requirements set by each use scenario. It 202 may exhibit e.g. a rectangular, circular, or square general shape. It may be free of recesses, cuts or openings such as holes/through-holes, or contain such for providing e.g. access to the elements provided on the substrate 202, on either side thereof. For example, for a battery change or UI feature (e.g. touch-sensitive area, button or switch) access the substrate 202 could be provided with related access route.

The item 204 refers to electronics provided on at least one side of the substrate film 202. The electronics 204 preferably comprises a number of active components and optionally passive components. The electronics 204 comprises e.g. controlling electronics, such as at least one integrated circuit (IC) for the sensing function utilizing a number of sensor pad areas 208 printed on the substrate 202 according to a predefined configuration and connected to the electronics 204 via intermediate conductors 205 such as printed conductor traces. Preferably each area 208 is served by at least one conductor trace 205. Suitable conductive ink, paint or adhesive may have been utilized in establishing the pads 208 and traces 205 that may basically thus appear as thin layers of conductive material on the substrate 202.

Optionally, the electronics 204 may include a number of further sensors or sensing functionalities, such as an accelerometer, temperature sensor, thermistor, etc.

The electronics 204 may include at least one element selected 5 from the group consisting of: a microcontroller, microprocessor, signal processor, DSP (digital signal processor), programmable logic chip, memory 207, transistor, resistor, capacitor, inductor, memory array, memory chip, data interface, transceiver, wireless transceiver, transmitter, receiver, wireless transmitter, and wireless receiver.

The electronics 204 may thus functionally include at least one processing unit with internal or external memory for storing instructions and other data, such as data captured by the pads 208 and/or derived using such data, and/or data provided by other sensing features. The data may be stored. It may also be transferred to an external entity such as a tablet, phablet, wristop device, some other type of a computer device or even a network service/infrastructure. The data may be first transferred to a near-by entity such as a tablet, phablet or mobile device, where it may be stored, processed, analysed and/or transmitted forward e.g. to a network service, or server, or other entity reachable via a network connection or generally communications connection.

The electronics 204 may include a data interface 213. For transferring data to external elements a transceiver or a transmitter may be implemented. For receiving data, such as program control parameters, control instructions, software update, data requests, etc. a transceiver or receiver may be implemented. The communication in either direction may be wired or wireless, optionally using RF (Radio Frequency) or inductive coupling based technology. Proprietary technology may be applied. Alternatively, e.g. selected Bluetooth™ (standard or low-power), RFID (Radio Frequency Identification), NFC (Near Field Communication) or other shortrange wireless communication standard may be followed. The technology may optionally be passive, i.e. the remote element such as phablet, smartphone or tablet may energize the transceiver or transmitter of the structure and enable data transmission therefrom.

In some embodiments, the data interface 213 may be integrated with power supply element described in more detail hereinafter.

Different sensing and/or other functionalities may be implemented by dedicated ICs, decicated components, or shared ICs/electronics (multi-purpose electronics).

The electronics 204 may include printed electronics obtained by printed electronics technology such as screen printing or ink jetting. Additionally or alternatively, the electronics 204 may include e.g. surface-mounted elements. For example, adhesive may be utilized for mechanically securing the electronics 204 on the substrate. Conductive materials such as adhesive and/or solder may be applied for establishing electrical and also mechanical connections.

Items 216A and 216B refer to a power supply element. The power supply element 216A, 216B may include a battery or at least a battery tray or bay for such. The battery may be disposable or rechargeable. A passage and e.g. hatch may be provided to reach and change the battery by shaping and/or dimensioning the substrate 202 and/or further layers accordingly.

In some embodiments the power supply element may include at least one element or component 216B such as a connector and/or wiring, or a battery, at the periphery of the structure 200 enabling the coupling of external power source, e.g. a battery. In these or some other embodiments, the power supply element may comprise component(s) 216A that are located in closer connection with the electronics 204 requiring the power supply. Intermediate wiring or e.g. conductive traces may be utilized to electrically connect items 216A, 216B in case both are implemented.

In some embodiments, energy harvesting component such as a piezo-electric transducer may be incorporated in the power supply element 216A, 216B.

In some embodiments, at least part if not all of the electronics 204 and optionally e.g. the power supply element 216A have been molded within at least two nested layers of material 206A, 206B, preferably plastics. The materials 206A and 206B may be mutually same or different.

Nevertheless, preferably at least one molded layer 206B has been provided on the substrate 206B such that it covers also the electronics 204 and optionally the power supply element 216A. The molded layer 206B may extend substantially over the whole substrate 202. It may further have substantially planar (upper) surface facing the direction opposite to the underlying electronics. Alternatively, the surface may be shaped so as to exhibit a desired three-dimensional shape with recesses and protrusive parts. Such 3d-forms may be configured to conveniently accommodate, conform to, and/or support e.g. a human foot sole in the context of insole/sole type application. In some other use scenarios, the forms could be configured to best cooperate the shapes of the contacting element, e.g. a liner or shell of a helmet.

The flexible substrate 202 may be overmolded by the layer 206B using injection molding by placing the substrate as an insert into a mold whereto the material establishing the layer 206B is shot. Optionally, a multi-shot molding procedure may be applied with multiple molded layers and optionally materials.

The material(s) of the layers 206A, 206B may include material(s) similar to the substrate film 202, e.g. thermoplastic, elastomer and/or polymer material such as PMMA. The materials may include elastic, flexible material that exhibits predetermined flexibility and e.g. cushioning properties to fit the target installation environment well and/or to add to a user experience e.g. in the context of footwear or headwear when the materials may directly or indirectly connect to a human body or particularly skin.

Optionally, at least part of the electronics 204 and optionally the power supply element 216A have been provided as a sub-assembly or sub-system on the substrate 202. The sub-assembly may have been prepared on a separate, 'secondary', substrate 202B first, whereupon the secondary substrate 202B and the related electronics have been as an ensemble provided onto the substrate 202 and secured thereto both electrically and mechanically. For example, adhesive, solder, conductive adhesive, etc. may have been used to bonding in addition to or instead of e.g. heat and/pressure—utilizing fixing procedure. Optionally, the sub-assembly has been overmolded 206A prior to installing it on the substrate 202. Alternatively, such optional overmolding 206A could take place after disposal on the substrate 202.

Underneath the substrate 202 at least one further layer 210 such as a protective and/or insulating layer may be provided. The layer 210 may optionally contain openings for providing access to the substrate and elements, such as the battery or UI, thereof.

Likewise, at least one top layer 212 may be provided. The top layer 212 may have a protective function, aesthetic function, insulating function, cushioning/dampening function, tactile function (provision of desired feel and/or friction characteristics) and e.g. aesthetical function. The layer 212 may include material already mentioned hereinbefore. It may further include e.g. textile, biological (e.g. leather) or rubber or rubbery type of material. Nevertheless, the layer(s) 212, if present, shall be dimensioned and also material-wise configured so as to enable capacitive sensing and potential other sensing method used in connection with the present invention.

Reverting to the measurement of capacitance, the capacitance, change in capacitance or 'relative' capacitance, for instance, may be determined by the suggested arrangement as the number of pads 208 may be provided as at least one layer (optionally pads 208 could be arranged in a three-dimensional configuration, e.g. in several overlapping layers) defining a number of electrodes 209 capacitively coupled with the user's conductive body or other conductor through an insulator, in this case at least the molded layer 206B. A voltage is to be applied to the pads 208 resulting in an electrostatic field, whereupon bringing a conductor 214 such as human sole, finger, etc. in the vicinity of the pads 208, a capacitor is formed. Change in the measured capacitance is then responsive to the location such as distance of the conductor relative to the pads 208. The conductor may be further positioned in the lateral direction, i.e. substantially along the plane defined by the substrate film 202 through provision of multiple pads 208 spatially distributed in that plane and by monitoring the associated capacitances. Thus at least pad level resolution may be obtained for positioning the capacitance/pressure indications.

Alternatively or additionally, a single pad (area), instead of considering it as a single electrode or an area served by a single electrode, could be electrically served by multiple electrodes (conductors independently connected to the voltage source) so that the positioning could be based on monitoring the individual electrodes (e.g. electrode currents) connected to the same pad.

Accordingly, the suggested structure may be configured to, depending on the embodiment, to detect, besides capacitance changes indicative of e.g. pressure (changes), also movements, weight transfer, stance and various other parameters derivable utilizing the same data. When further sensors are implemented by the structure, further variables may become available for monitoring. For example, temperature sensor may provide temperature data and accelerometer acceleration data and data derivable therefrom, such as speed data.

The layers 210 and 212 have been depicted as separate from the substrate 202 and molded plastics 206B for clarity reasons. In practical circumstances, the layers 210, 212 may be connected to the substrate 202 and plastics 206B, by a suitable lamination or molding technique. E.g. adhesive, heat and/or pressure may be utilized.

Figure 3:
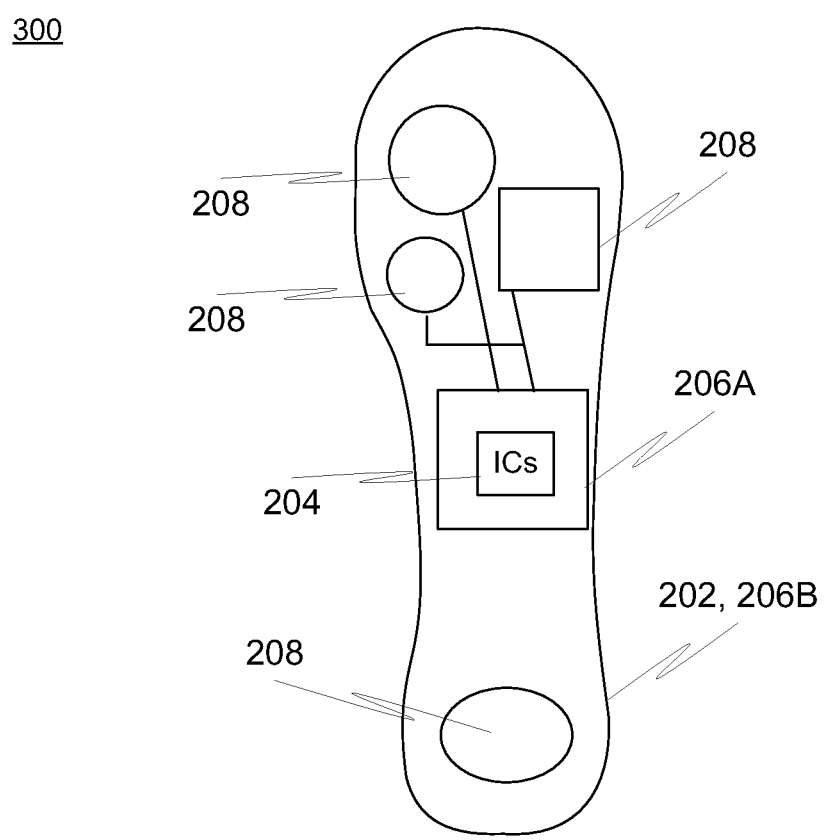
FIG. 3 illustrates, via a cross-sectional front or top view, one embodiment of the present invention in a footwear context.

FIG. 3 illustrates, via a cross-sectional top view 300, one embodiment of the present invention in a footwear context. The multilayer structure in accordance with an embodiment of the present invention, such as the embodiment of FIG. 2, may establish at least part of a shoe sole or insole. A plurality of sensor pad areas 208, optionally of mutually different size and/or shape, may be printed on the substrate. A voltage may be supplied to them to establish electrodes for capacitive sensing.

Different areas of the human sole may be addressed with dedicated sensor pads 208 of the structure. For example, a ball area or some other predefined area of the user's foot may be addressed with at least one dedicated, location-wise matching pad 208 (see the upper pads in the figure for conceptual reference) on the substrate whereas e.g. the heel area could be provided with at least one other dedicated pad 208 (see the lowermost pad 208 in the figure).

Accordingly, in addition to generic characteristics derivable using the sensor data by a single sensor pad only, or multiple sensor pads considered as an aggregate, such as overall or average pressure subjected to the sole/insole by the human sole pressure distribution, distribution changes, stance, etc. may be deduced from the data. Even pediatric conditions, optionally flat feet, could be deduced based on the data.

Figure 4:
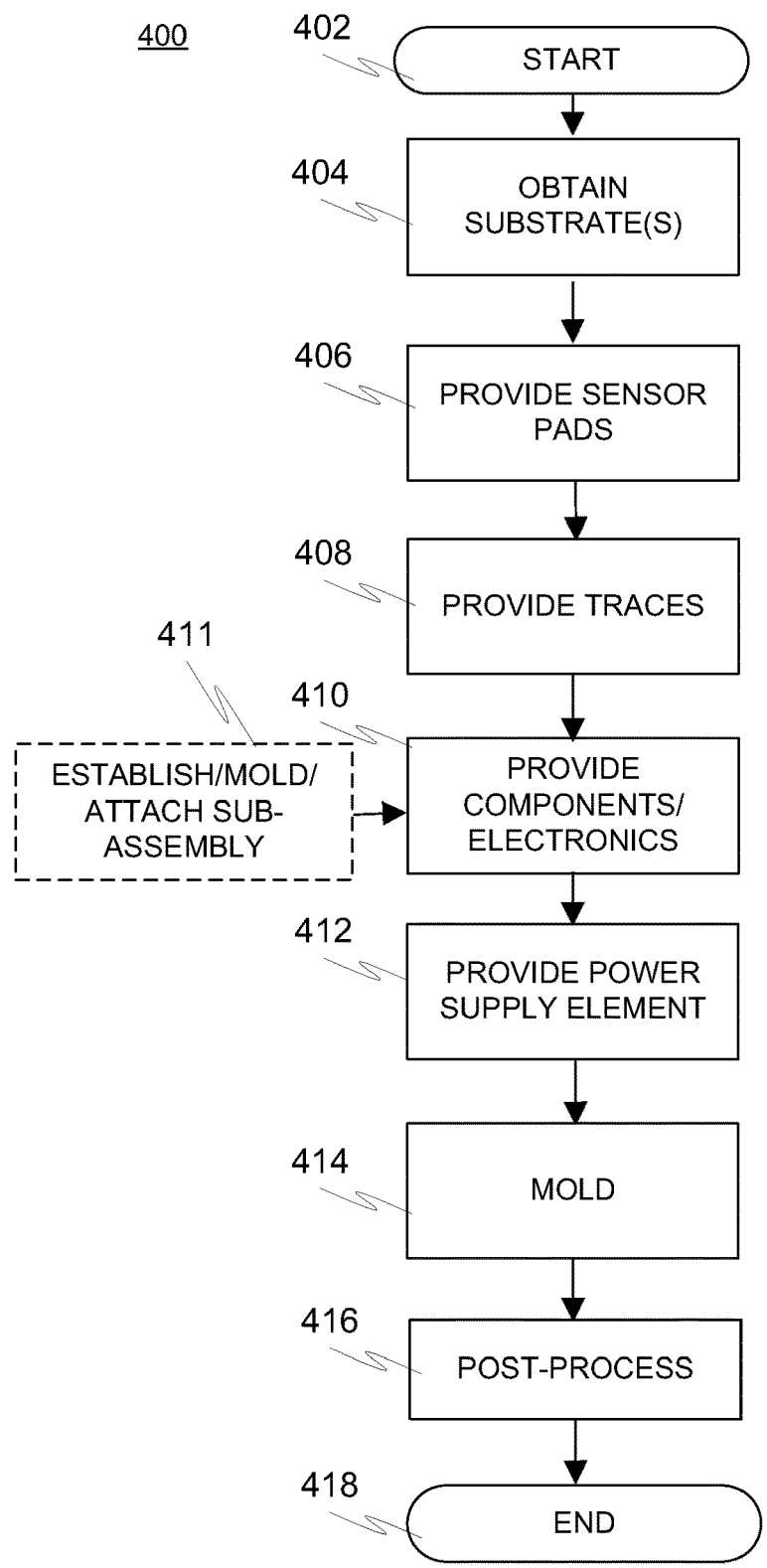
FIG. 4 is a flow diagram disclosing an embodiment of a method in accordance with the present invention.

FIG. 4 includes a flow diagram 400 disclosing an embodiment of a method in accordance with the present invention.

At the beginning of the method for manufacturing a stacked, multilayer structure, a start-up phase 402 may be executed. During start-up 402, the necessary tasks such as material, component and tools selection, acquisition, calibration and other configuration may take place. Specific care must be taken that the individual elements and material selections work together and survive the selected manufacturing and installation process, which is naturally preferably checked up-front on the basis of the manufacturing process specifications and component data sheets, or by investigating and testing the produced prototypes, for example. The used equipment such as molding/IMD (in-mold decoration), lamination, bonding, thermoforming, and/or printing equipment, among others, may be thus ramped up to operational status at this stage.

At 404, at least one, preferably flexible, substrate film for accommodating electronics is obtained. A ready-made element of substrate material, e.g. a roll of plastic film, may be acquired. In some embodiments the substrate film itself may be in-house produced from scratch by molding or other methods from the desired starting material(s). Optionally, the substrate film is processed. It may be, for example, provided with openings, recesses, cuts, etc. for enabling e.g. the provision of electrically and/or optically conductive connections therethrough.

At 406 one or more sensor pads are printed on the substrate. A predefined area on the substrate surface coated with printed conductive material such as ink or paint may establish a pad. For example, screen, inkjet, flexographic, gravure or offset lithographic printing may be utilized.

Different electrical elements such as pads, control electronics and optionally power source element may be functionally connected using printed traces of conductive material such as ink.

Accordingly, at 408 a number of conductor traces are provided on the film for powering a number of electricity-driven components such as the pads. One or both sides of the substrate film may be configured to accommodate pads. Preferably at least the side facing, when in use, the external element(s) the effect of which is to be monitored via the pad-based measurements, such as a foot sole, is provided with one or more pads. In the footwear application, that side would be the predefined top side of the sole/insole facing the user's foot.

Depending on the material of the substrate (examples of different applicable materials have already been listed hereinbefore) the traces may be formed using a suitable technique, preferably printed electronics based technique such as screen printing or ink jetting. Alternatively, e.g. etching-based method could be considered.

At 410, electronics such as the electronics circuit, optionally one or more IC(s), for controlling e.g. the measurements utilizing the printed pads are provided. One or both sides of the substrate film may be configured to accommodate electronics. Again, printed electronics technology may be applied to actually manufacture at least part of the components directly onto the film. Alternatively or additionally, a number of ready-made components such as SMD(s) (surface-mount device) and/or passive components may be configured to the film. Adhesive may be utilized for mechanical attachment, whereas solder and conductive ink are feasible for making electrical connections between elements.

Item 411 refers to optional attachment of one or more sub-systems or 'sub-assemblies' that may incorporate an initially separate, secondary substrate provided with electronics such as IC(s) and/or various components. At least part or all of the electronics of the multilayer structure may be provided to the substrate film via such sub-assembly. Optionally, the sub-assembly may be at least partially overmolded by a protective plastic layer prior to attachment to the main substrate. For example, adhesive, pressure and/or heat may be used for mechanical bonding of the sub-assembly with the primary (host) substrate. Solder, wiring and conductive ink are examples of applicable options for providing the electrical connections between the elements of the sub-assembly and with the remaining electrical elements on the primary substrate.

At 412, a power supply element, such as a battery and related conductors, and/or a connector for external power source with necessary wiring, is provided to arrange power to at least part of the electronics, when the structure is in use. Optionally, the battery is of rechargeable type and may be recharged using external power supply. In some embodiments, a number of energy harvesting elements may be provided in the structure for providing energy to the electronics and/or recharging the battery. Such harvesting elements may include e.g. piezoelectric or thermoelectric transducers.

At 414, at least one plastic layer is molded upon the substrate film and electronics thereon. The substrate film may be substantially covered by the plastics on one or both sides.

In some embodiments, prior to or upon the molding phase the substrate film optionally already containing electronics may be thermoformed. The substrate containing thermoformable material may be shaped to better fit the target environment, e.g. inside footwear, helmet or some other host garment such as a shirt, e.g. compression shirt, (compression) shorts or generally (compression) trousers. Alternatively or additionally, it may be shaped to receive e.g. human sole ergonomically.

Regarding the resulting overall thickness of the obtained stacked structure, it heavily depends on the used materials and related minimum material thicknesses providing the necessary strength in view of the manufacturing and subsequent use. These aspects have to be considered on case-by-case basis. For example, the overall thickness of the structure could be about 1 mm, but thicker or thinner embodiments are also fully feasible.

Item 416, refers to possible post-processing tasks. Further layers may be added into the multilayer structure. The structure may be installed at a host device or host element such as a piece of footwear, helmet, compression garment, other garment, etc.

Item 418 refers to the ending phase of the method.

A skilled person will appreciate the fact the execution order of various method items may be changed depending on the embodiment and use scenario. For example, in some embodiments traces 408 may be provided prior to the pads 406, or they may be produced alternately. Yet, power supply element(s) 412 may be provided prior to or in connection with (other) electronics 410.

The scope of the present invention is determined by the attached claims together with the equivalents thereof. A person skilled in the art will appreciate the fact that the disclosed embodiments were constructed for illustrative purposes only, and the innovative core of the suggested solution reviewed hereinbefore will cover further embodiments, embodiment combinations, variations and equivalents that better suit each real-life use case. Regarding the provided multilayer structure, in some embodiments the construction may, for instance, include a plurality of substrates and/or overlying plastic layers instead of merely one instance per layer type. Similar layers may be adjacent to each other, have different layer(s) in between, or establish some other configuration in the multilayer structure. A number of further layers not explicitly reviewed hereinbefore may be included in the structure as well, e.g. a thermally, electrically, chemically, or otherwise insulating/blocking, conductive or active layer. In some contexts, sensor pads and/or conductor traces could be provided using techniques other than the ones of printed electronics. For example, deposition (or some other additive technique) and etching (or some other subtractive technique) could be considered.

The invention claimed is:

1. A method for manufacturing a multilayer structure, the method comprising:
   printing a plurality of flexible sensor pads on a flexible substrate film;
   printing conductor traces on the flexible substrate film to electrically connect each flexible sensor pad of the plurality of flexible sensor pads with an electronic circuit, each conductive trace connecting one of the plurality of flexible sensor pads with the electronic circuit;
   providing the electronic circuit on the flexible substrate film to control capacitive measurements via the plurality of flexible sensor pads to obtain an indication of pressure subjected to the multilayer structure and to monitor a capacitance between each flexible sensor pad of the plurality of flexible sensor pads and a sole of a user placed upon the structure and functionally forming a capacitor with the at least one flexible sensor pad of the plurality of flexible sensor pads the electronic circuit overmolded with a first material layer after the electronic circuit is provided on the flexible substrate;
   attaching a Surface-Mount Device (SMD) to the flexible substrate film;
   providing a power supply element for supplying electricity-driven components including the electronic circuit with electricity; and
   molding a second material layer being a plastic layer upon the flexible substrate film substantially embedding the plurality of flexible sensor pads, the conductor traces, the SMD, and the electronic circuit therewithin.

2. The method according to claim 1, wherein printing the plurality of flexible sensor pads includes printing a first flexible sensor pad at a location remote to the SMD.

3. The method according to claim 1, wherein printing the plurality of flexible sensor pads on the flexible substrate film includes the flexible substrate film being free of recesses, cuts, and openings.

4. A method of manufacturing a garment, the method comprising:
   printing a plurality of flexible sensor pads on a flexible substrate film;
   printing a conductor traces on the flexible substrate film to electrically connect each flexible sensor pad of the plurality flexible sensor pads with an electronic circuit;
   providing the electronic circuit on the flexible substrate film to control capacitive measurements via the plurality of flexible sensor pads to obtain an indication of pressure subjected to the multilayer structure and to monitor a capacitance between the each flexible sensor pad of the plurality of flexible sensor pads and a sole of a user placed upon the structure and functionally forming a capacitor with the at least one flexible sensor pad of the plurality of flexible sensor pads the electronic circuit overmolded with a first material layer after the electronic circuit is provided on the flexible substrate;
   attaching a Surface-Mount Device (SMD) to the flexible substrate film;
   providing a power supply element for supplying electricity-driven components including the electronic circuit with electricity;
   molding a second material layer being a plastic layer upon the flexible substrate film substantially embedding the number of flexible sensor pads, the conductor traces, the SMD, and the electronic circuit therewithin; and
   integrating the flexible substrate film into a garment.

5. The garment according to claim 4, wherein the garment is a compression garment.

6. The garment according to claim 4, wherein the garment is footwear.

7. The garment according to claim 6, wherein printing the plurality of flexible sensors includes printing a first flexible sensor pad positioned in a ball area of the footwear and printing a second flexible sensor pad in a heel area of the foot wear such that the first and second flexible sensor pads are spaced apart from one another.

8. A multilayer structure comprising:
a flexible substrate film;
a plurality of flexible sensor pads printed on the flexible substrate film;
an electronic circuit further provided on the flexible substrate film to control capacitive measurements via the plurality of flexible sensor pads to obtain an indication of pressure subjected to the multilayer structure and to monitor a capacitance between each flexible sensor pad of the plurality of flexible sensor pads and a sole of a user placed upon the structure and functionally forming a capacitor with at least one flexible sensor pad of the plurality of flexible sensor pads;
conductor traces printed on the flexible substrate film to electrically connect the electronic circuit and flexible sensor pads of the plurality of flexible sensor pads, the electronic circuit and a portion of the conductor traces overmolded with a first material layer;
a Surface-Mount Device (SMD) attached to the flexible substrate film;
a power supply element for powering electricity-driven components including the electronic circuit; and
a second material layer being a plastic layer molded upon the flexible substrate film substantially embedding the plurality of flexible sensor pads, the conductor traces, the SMD, and the electronic circuit therewithin, the SMD configured to be attached to the flexible substrate film as the at least one plastic layer is molded upon the flexible substrate film.

9. The structure according to claim 8, wherein the plurality of flexible sensor pads comprises a substantially two-dimensional configuration of flexible sensor pads over the flexible substrate film, to enable positioning the indication of pressure.

10. The structure of claim 8, wherein a first flexible sensor pad of the plurality of flexible sensor pads is provided with a plurality of electrodes to enable positioning the indication of pressure within a sensor area defined by the first flexible sensor pad.

11. The structure of claim 8, wherein the electronic circuit comprises an integrated circuit incorporating at least one of a microcontroller, a microprocessor, a programmable logic chip, or a signal processor.

12. The structure of claim 8, wherein the electronic circuit comprises memory configured to store measured data or data derived therefrom.

13. The structure of claim 8, wherein the electronic circuit comprises a data interface for communication with an external electronic element.

14. The structure of claim 8, wherein the power supply element comprises at least one element selected from the group consisting of:
a battery, a disposable battery, a replaceable battery, a connector for a battery, a connector for coupling with an external power supply, an energy harvesting element, and a piezoelectric transducer.

15. The structure of claim 8, wherein at least part of the electronic circuit defines and has been provided as a subassembly with an initially separate substrate.

16. The structure of claim 8, further comprising an initial plastic layer molded upon at least part of the electronics of the electronic circuit to protect the at least part of the electronics embedded therewithin during the molding of the plastic layer.

* * * * *